(12) United States Patent
Ridall et al.

(10) Patent No.: US 10,695,332 B2
(45) Date of Patent: *Jun. 30, 2020

(54) PHARMACEUTICAL COMPOSITIONS FOR DIRECT SYSTEMIC INTRODUCTION

(71) Applicant: NewMarket Pharmaceuticals LLC, Trenton, NJ (US)

(72) Inventors: Mark Ridall, Princeton, NJ (US); David Rock, Hillsborough, NJ (US)

(73) Assignee: NewMarket Pharmaceuticals LLC, Trenton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,407

(22) Filed: Aug. 30, 2018

(65) Prior Publication Data

US 2018/0369221 A1 Dec. 27, 2018

Related U.S. Application Data

(63) Continuation of application No. 14/398,085, filed as application No. PCT/US2012/070031 on Dec. 17, 2012, now Pat. No. 10,064,849.

(60) Provisional application No. 61/641,509, filed on May 2, 2012, provisional application No. 61/674,435, filed on Jul. 23, 2012, provisional application No. 61/678,355, filed on Aug. 1, 2012.

(51) Int. Cl.
| | |
|---|---|
| *A61K 9/20* | (2006.01) |
| *A61K 31/4439* | (2006.01) |
| *A61K 9/00* | (2006.01) |

(52) U.S. Cl.
CPC .......... *A61K 31/4439* (2013.01); *A61K 9/006* (2013.01); *A61K 9/0056* (2013.01); *A61K 9/2013* (2013.01); *A61K 9/2018* (2013.01); *A61K 9/2063* (2013.01); *A61K 9/2095* (2013.01)

(58) Field of Classification Search
CPC .............................. A61K 9/20; A61K 31/4439
See application file for complete search history.

(56) References Cited

U.S. PATENT DOCUMENTS

| | | |
|---|---|---|
| 6,193,999 B1 | 2/2001 | Gennadios |
| 6,471,992 B1 | 10/2002 | Yoo et al. |
| 6,596,311 B1 | 7/2003 | Dobetti |
| 6,709,669 B1 | 3/2004 | Murray |
| 7,122,198 B1 | 10/2006 | Singh et al. |
| 7,939,561 B2 | 5/2011 | Schellenger et al. |
| 8,545,879 B2 | 10/2013 | Burns et al. |
| 8,647,668 B2 | 2/2014 | Tanaka et al. |
| 8,722,636 B2 | 5/2014 | Rock et al. |
| 9,402,835 B2 | 8/2016 | Rock et al. |
| 10,022,361 B2 | 7/2018 | Rock et al. |
| 10,064,849 B2 | 9/2018 | Ridall et al. |
| 2002/0035076 A1 | 3/2002 | Parks |
| 2003/0031711 A1 | 2/2003 | Fara et al. |
| 2004/0248942 A1 | 12/2004 | Hepburn et al. |
| 2007/0042023 A1 | 2/2007 | Puri et al. |
| 2007/0275058 A1 | 2/2007 | Tanaka et al. |
| 2007/0184106 A1 | 8/2007 | Schellenger et al. |
| 2008/0096971 A1 | 4/2008 | Baxter et al. |
| 2011/0256229 A1 | 10/2011 | Nystrom et al. |
| 2012/0219628 A1 | 8/2012 | Lim et al. |
| 2015/0133504 A1 | 5/2015 | Ridall et al. |
| 2018/0360816 A1 | 12/2018 | Rock et al. |
| 2018/0369221 A1 | 12/2018 | Ridall et al. |

FOREIGN PATENT DOCUMENTS

| | | |
|---|---|---|
| CA | 2369951 A1 | 11/2000 |
| EP | 1 891 937 A1 | 2/2008 |
| WO | 00/50038 | 8/2000 |
| WO | 02/058735 A1 | 8/2002 |
| WO | 2004/067004 A1 | 8/2004 |
| WO | 2006/048501 A1 | 5/2006 |
| WO | 2007/002125 A1 | 1/2007 |
| WO | 2012106058 | 8/2012 |
| WO | 2013165468 | 11/2013 |

OTHER PUBLICATIONS

Extended European Search Report in EP 12875765 (corresponds to PCT/US2012/070031) dated Aug. 31, 2015.
Arvanitoyannis et al., "Edible films made from hydroxypropyl starch and gelatin and plasticized by polyols and water," Carbohydrate Polymers 36:105-119 (1998).
International Search Report in PCT Application No. PCT/US2012/070031 dated Feb. 26, 2013.
International Preliminary Report on Patentability in PCT Application No. PCT/US2012/070031 dated Nov. 13, 2014.

(Continued)

*Primary Examiner* — Zohreh A Fay

(74) *Attorney, Agent, or Firm* — Cadwalader, Wickersham & Taft LLP

(57) ABSTRACT

The invention relates to pharmaceutical compositions for direct systemic introduction, are also known as DSI pharmaceutical compositions, for used as human veterinary pharmaceutical compositions. In one embodiment, the invention relates to a pharmaceutical composition for direct system introduction comprising bovine gelatin, mannitol, an optional surfactant, an optional flavorant, and an active pharmaceutical ingredient. A DSI pharmaceutical composition of the invention has a disintegration time of 7 seconds or less in deionized water maintained at 37.0° C.±0.5° C. The invention also relates to a method of delivering an active pharmaceutical ingredient to an animal comprising the step of placing a DSI pharmaceutical composition of the invention into a mucosal cavity of an animal to be treated with the active pharmaceutical ingredient and to the corresponding methods of treatment.

17 Claims, 1 Drawing Sheet

(56) References Cited

OTHER PUBLICATIONS

Chubineh et al.: "Proton Pump Inhibitors: the Good the Bad and the Unwanted," Southern Medical Journal, vol. 105, No. 11, pp. 613-618, Nov. 2012.
Glossary of Medical Education Terms, Intstitute of International Medical Education. http://www.iime.org/glossary.htm Accessed on Jan. 2013.
International Search Report for International Application No. PCT/US2012/020242 dated Aug. 30, 2012 (corresponds to WO 2012/106058).
International Preliminary Report on Patentability for International Application No. PCT/US2012/020242 dated Aug. 6, 2013 (corresponds to WO 2012/106058).
Liles et al. The use of non-steroidal anti-inflammatory drugs for the relief of pain in laboratory rodents and rabbits. Laboratory Animals 26:241-255, 1992.
Mona Nagar et al.: "Formulation, Evaluation and Comparison of Fast-Dissolving Tablet of Nimesulide by Using Crospovidone as Superdisintegrant," International Journal of Pharmaceutical Sciences and Drug Research, 2009, 1(3), pp. 172-175.
R. Panigrahi et al.: "A Review on Fast Dissolving Tablets," WebMedCentral Pharmaceutical Sciences, Sep. 29, 2010, 1(9), pp. 1-15.
www.avma.org/isues/drugs/compouncing/veterinary_compounding_brochure.asp, Veterinary Compounding Brochure, American Veterinary Medical Association (AVMA) Jun. 2001.
www.fda.gov/AnimalVeterinary/NewsEvents/FDAVeterinarian-Newsletter/ucm10026- 8.htm, Mar./Apr. 2003.

PHARMACEUTICAL COMPOSITIONS FOR DIRECT SYSTEMIC INTRODUCTION

CROSS REFERENCE TO RELATED APPLICATIONS

This application is a Continuation of U.S. application Ser. No. 14/398,085, filed Oct. 30, 2014; which claims priority to PCT International Application No. PCT/US2012/070031, filed Dec. 17, 2012; which claims priority to U.S. Provisional Application No. 61/641,509, filed May 2, 2012; U.S. Provisional Application No. 61/674,435, filed Jul. 23, 2012; and U.S. Provisional Application No. 61/678,355, filed Aug. 1, 2012; the disclosures of which are incorporated herein by reference.

BACKGROUND

The delivery of therapeutic agents for animals, for example humans, equines, bovines, canines, felines, ovines, and porcines suffer from numerous serious disadvantages for a variety of reasons. Injectable formulations, which typically provide rapid onset of activity, are most preferably administered in an environment of cleanliness to prevent infections entering the injection site. But, this is difficult to ensure outside of a clinical setting. And cleanliness is nearly impossible to ensure in a typical horse barn, farm, field or racetrack. Along with this rapid onset of activity, an injectable therapeutic typically suffers from a relatively short and single-peaked Time versus Blood Concentration profile.

Conventional oral dosing of animals also suffers from a variety of disadvantages. For example, the animal can spit out the formulation, resulting in a loss of the full dosage. Also, if administered by intubation, the bioavailability can vary considerably due to the inherent and unique characteristics of each animal's digestive system, i.e., the amount of food in the animal's stomach, the length of time since its last feeding, and the animal's levels of digestive enzymes, which may vary due to other environmental conditions, etc. Also, the active ingredient in the oral formulation is sometimes unstable. In some cases the active ingredient in an oral formulation may be unstable because of the pH and/or digestive materials present in an animal's stomach. Moreover, administering conventional oral dosages forms to an animal, e.g., a horse, creates the risk of inadvertently dosing the human administrator with the drug substance.

Another disadvantage of many oral and injectable formulations is that those formulations require administering a relatively high mass percentage ("mass %") of inactive material to the animal. For example, many oral and injectable formulations comprise significant amounts of carriers and/or excipients that provide no direct benefit to the animal. Many care providers generally agree that animals should not consume unnecessary pharmaceutical substances. Accordingly, it would be advantageous to minimize the amount of non-therapeutic materials administered to an animal when providing the pharmaceutically active substance. For example, when providing omeprazole to an animal in need thereof, many conventional formulations comprise more than 50% of an inactive substance having no therapeutic effect. Conventional oral formulations of omeprazole may also often suffer from the disadvantageous correlation between bioavailability and the contents of the animal's stomach. For example, bioavailability may be lessened on account of the animal having food present in its stomach.

Fast release pharmaceutical formulations have been disclosed in the art. These may include multi-particulate fast disintegrating tablets as disclosed, for instance in U.S. Pat. No. 6,596,311; the so-called rapidly dispersing "3-D platform", disclosed in U.S. Pat. No. 6,471,992; and pectin-based dissolvable films, such as disclosed in US2007/0042023. Immediate release compositions are disclosed WO 2012/106058. Each of these disclosures is incorporated herein by reference.

Still, there exists a need in the art to provide improved therapeutic methods for animals (for example humans, equines, bovines, ovines, canines, felines and porcines) which obviate many of the disadvantages and side effects of the commonly used injectable and oral formulations.

There is also a need in the art to provide methods for the treatment of humans, equines, bovines, canines, felines, ovines, and porcines equines with drug products which give an earlier onset of action, reduce the number and severity of side effects, lessen the risk of infection at injection sites, and mitigate the bioavailability issues incident to administering the drug via absorption within the digestive tract of the animal.

There is a still another need in the art to provide methods which enable treatment of the animal patient that provide more reliable and predictable clearance from the animal.

The invention disclosed here answers one or more of these needs discussed above. The features, objects, and advantages of the disclosed invention will be apparent to those skilled in the art from the description of the invention, and from the claims.

SUMMARY OF THE INVENTION

The invention relates to pharmaceutical compositions for direct systemic introduction (DSI), which are also known as DSI pharmaceutical compositions. DSI pharmaceutical compositions may used in both as human pharmaceutical compositions and veterinary pharmaceutical compositions. Various DSI pharmaceutical compositions are described herein.

In one embodiment, the invention relates to a pharmaceutical composition for direct system introduction comprising: about 5-20 mass % bovine gelatin, about 5-20 mass % mannitol, about 0-1 mass % of a surfactant, about 0-0.5 mass % of a flavorant, and about 60-90 mass % of an active pharmaceutical ingredient. The pharmaceutical composition may comprise about 10-17 mass % bovine gelatin, about 10-17 mass % mannitol, and about 0-0.5 mass percent of a surfactant. Alternatively, the pharmaceutical composition may comprise about 10-13 mass % bovine gelatin, about 12-15 mass % mannitol, and about 0.1-0.3 mass % of a surfactant. Omeprazole is one active pharmaceutical ingredient that may be formulation in a pharmaceutical composition of the invention.

Another embodiment of the invention relates to a DSI pharmaceutical composition, such as described herein, having a disintegration time of 5 seconds or less in deionized water maintained at 37.0° C.±0.5° C. A DSI pharmaceutical composition of the invention may have a disintegration time of 3 seconds or less in deionized water maintained at 37.0° C.±0.5° C.

The invention also relates to a method of delivering an active pharmaceutical ingredient to an animal comprising the step of placing a DSI pharmaceutical composition of the invention into a mucosal cavity of an animal to be treated with the active pharmaceutical ingredient. The invention also relates to various methods of treatment administering an active pharmaceutical ingredient in this manner.

DETAILED DESCRIPTION

Figure 1:
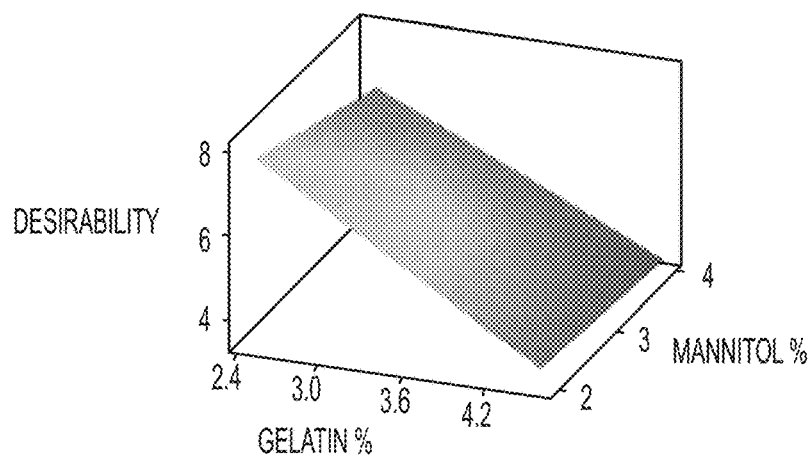
FIG. 1 depicts the DOE Response surface of Factors 1 & 2 (Factor 3 fixed at 15° C. shelf temperature) as described in Example 3.

Disclosed herein are pharmaceutical compositions and methods for treating animals, for example humans, equines, bovines, canines, felines, ovines, and porcines. Various embodiments comprise administering an active pharmaceutical ingredient, also known as a therapeutic agent, into the bloodstream of the animal by introducing it transdermally across the animal's non-keratinous fibers, e.g., via the oral cavity, anal cavity, vaginal cavity, nasal cavity, gingival mucosa, lingual mucosa, palatal mucosa, pharyngeal mucosa, sublingual mucosa, and/or non-gastric mucosa. In various embodiments, a majority of the formulation may be absorbed prior to reaching the gastric mucosa. In certain embodiments, the formulation may be adapted for animals, for example humans, equines, bovines, canines, felines, ovines, and porcines to dissolve in a relatively short period of time, e.g., 90 seconds or less.

In some embodiments, administering a DSI pharmaceutical composition of the invention provides for faster onset of the therapy, diminished occurrences of the side-effects due to nonuniformity of bioavailability of the active pharmaceutical ingredient, and/or more accurate dosing. In at least some embodiments, these features result in dose lowering. Further, in at least some embodiments, such administration may result in a greater portion of the therapeutic agent actually being directly introduced systemically into the circulatory system for its therapeutic effect. For example, in the case of omeprazole, the DSI pharmaceutical compositions disclosed herein provide an advantage because the bioavailability of omeprazole is not limited by the presence of matter (e.g., food) in the animal's stomach. For example, the disclosed methods of administering the active pharmaceutical ingredient omeprazole do not require fasting the animals prior to administering omeprazole. And the bioavailability of omeprazole is not compromised by the contents of the animal's stomach.

Also disclosed herein are methods for the treatment and control of various diseases afflicting animals, for example equines, bovines, canines, felines, ovines, and porcines, with improved safety for the both the animal and the person administering the therapeutic agent. In at least certain exemplary embodiments, the compositions and methods are useful for administration to humans. For example, disclosed herein are methods of treating gastroesophageal reflux disease, gastritis, peptic ulcer disease, dyspepsia, laryngopharyngeal reflux, Zollinger-Ellison syndrome, duodenal ulcers and/or preventing gastric ulcers (e.g., gastric ulcers associated with NSAID therapy or Chrohn's disease) and/or controlling the production of digestive fluids (e.g., gastric acids) and/or normalizing the pH of an animal's stomach comprising administering a DSI compound comprising one or more proton pump inhibitors (e.g., omeprazole and/or any of its stereoisomers).

Administering therapeutic agents to the animal without needles, via the non-keratinous tissues into a mucosal cavity, e.g., the oral cavity, anal cavity, vaginal cavity, nasal cavity, gingival mucosa, lingual mucosa, palatal mucosa, pharyngeal mucosa, sublingual mucosa, and/or non-gastric mucosa results in rapid onset of activity, more accurate dosing, lowered dosing, an absence or diminishment of side-effects, and greater safety to both the animal and the administrator of the formulation. In some cases the therapeutic agents may be administered via the animal's oral cavity, anal cavity, vaginal cavity, nasal cavity, gingival mucosa, lingual mucosa, palatal mucosa, pharyngeal mucosa, sublingual mucosa, and/or non-gastric mucosa.

As used herein, the term "oral cavity" means that portion of the alimentary canal from the orifice conventionally referred to as the mouth, including, for example the area distally from the mouth to the esophagus and all tissues including, for example under the tongue (sublingual), on the top of the tongue, and/or between the cheek and gums (buccal), the mucal membranes, epithelium, and gums.

As used herein, the term "non-gastric mucosa" refers to the pre-gastric mucosal cells, e.g., oral mucosa, including the mucous membrane beneath the tongue, and/or the buccal mucosa at the inside of the cheek and gum and absorption sites in the esopaghus.

As used herein, the term "pre-gastric" refers to all parts of the alimentary canal beginning at the mouth and continuing to the juncture with the first secretory stomach.

As used herein, "Direct Systemic Introduction" ("DSI"), means administering one or more therapeutically active agent directly to the circulatory system of an animal via a formulation administered and absorbed across non-keratinous fibers, e.g., the oral cavity and/or the non-gastric mucosa. DSI may, in at least some embodiments, provide relatively high systemic concentrations of the active agents, e.g. by allowing agents to pass directly into the systemic circulation avoiding the destructive activities in the digestive tract by gastric breakdown, metabolism in the wall of the GI tract and first pass metabolism by the liver. In one embodiment, administering a DSI pharmaceutical composition comprises contacting the animal's first secretory stomach with less than about 50% of the DSI pharmaceutical composition administered to the animal.

DSI may result in higher systemic availability of therapeutic agents in the animal for their desired therapeutic effects vis-á-vis products formulated in conventional oral delivery systems. DSI provides advantages over traditional oral, intravenous, intramuscular, and subcutaneous routes of administration, in that more of the drug may be available systemically for its desired therapeutic effects. For example, in equines, DSI can provide more rapid metabolic clearance of the drug, resulting in a shortened withdrawal time to clear the animal for performance racing. See, e.g., "Equine Drug Testing and Therapeutic Medication Regulation: 2009 Policy of the National Horsemen's Benevolent and Protective Association, Inc." edited by Thomas Tobin & Kent H. Stirling, which discusses the necessary withdrawal times for performance animals.

A DSI pharmaceutical composition of the invention disintegrates quickly in water. A DSI pharmaceutical composition of the invention generally has a disintegration time of 7 seconds or less in deionized water maintained at 37.0° C.±0.5° C. A DSI pharmaceutical composition of the invention may have a disintegration time of 4 seconds or less in deionized water maintained at 37.0° C.±0.5° C.

The raid dissolution of the DSI pharmaceutical compositions disclosed herein allows them to also dissolve rapidly when in contact with an animal's non-keratinous fibers/mucosal cavity, for example, the oral cavity and/or the non-gastric mucosa. In some embodiments, the formulations contemplated herein will dissolve when in contact with the animal's non-keratinous fibers, e.g., the oral cavity and/or the non-gastric mucosa in about 90 seconds or less. In some embodiments, the DSI pharmaceutical composition will dissolve in about 75 seconds or less, such as in about 60 seconds or less, about 45 seconds or less, about 30 seconds or less, about 20 seconds or less, about 10 seconds or less or about 5 seconds or less. In some embodiments, the DSI pharmaceutical composition dissolves in less than about 3 seconds.

A further benefit of the DSI dosing of an animal is that the person administering may be able to more quickly titrate an appropriate dosage for the level and severity of the condition of the animal. Using typical routes of administration, due to metabolic disposition and the overall health of the animal, it may take a practitioner a period of several days to achieve an appropriate dose to treat and control a condition. One advantage of a DSI pharmaceutical composition is that the practitioner may reliably assume therapeutic effects within a short period of time, and adjust the level of administration of the drug, as needed.

In at least some embodiments, DSI pharmaceutical compositions permit a shorter withdrawal time from treatment than with some conventional oral dosing regimens. By way of example only, typically, an equine patient will need to be withdrawn from many medications for periods ranging from 24-72 hours prior to performance racing. This results in interruption of the therapy, and can lead to a worsening of the existing disease, or at the least, a slower recovery than if the withdrawal had not occurred. In many cases using DSI therapy, however, the equine patient may only need to discontinue the therapy for a period as short as 0-12 hours or not at all, depending upon the particular therapeutic agent being utilized in the methods of the present disclosure.

In at least one exemplary embodiment, the methods herein are administered to the circulatory system of the animal via a DSI pharmaceutical composition administered and absorbed via the non-keratinous fibers/mucosal cavity, such as in the oral cavity and/or the non-gastric mucosa, adapted for humans, equines, bovines, canines, felines, ovines, and porcines, resulting in rapid absorption of the active ingredient and faster clearance. Due to both administration and absorption to the oral cavity and/or the non-gastric mucosa, the resultant effect is DSI.

In some embodiments, the oral dissolution of the disclosed DSI pharmaceutical compositions occurs without the addition of non-biological liquids or accelerants. For example, the DSI pharmaceutical compositions may disintegrate rapidly upon contact with the animal's biological fibers and/or biological fluids. In some embodiments, the DSI pharmaceutical compositions may be administered without the need for any additional sources of accelerant, dissolving agent, or contemporaneous drink.

In one embodiment, the DSI pharmaceutical composition comprises a proton pump inhibitor as the active pharmaceutical ingredient. As used in this application, the term "proton-pump inhibitor" (sometimes abbreviated "PPI") refers to a group of drugs that provide pronounced and long-lasting reduction of gastric acid production. Without being bound by any theory, proton pump inhibitors are believed to act by irreversibly blocking the hydrogen/potassium adenosine triphosphatase enzyme system (often described in terms of "the H+/K+ ATPase" or "gastric proton pump") of the gastric parietal cells. As used in this application, the term proton pump inhibitor includes but is not limited to omeprazole, lansoprazole, rabeprazole, pantoprazole, dexlansoprazole, esomeprazole, etc.

In one embodiment, the DSI pharmaceutical composition comprises omeprazole. In one embodiment, the DSI pharmaceutical composition comprises micronized omeprazole. As used herein, the term "micronized" means having an average particle diameter of between about $1 \times 10^{-3}$ to about $1 \times 10^{-7}$ meters. For example, in some embodiments the disclosed DSI pharmaceutical compositions comprising omeprazole are formulated with micronized omeprazole having an average particle diameter of about 1 to about 10 microns.

In one embodiment, the DSI pharmaceutical composition comprises both a proton pump inhibitor and an H2 blocker (also known as an H2 receptor antagonist). In one embodiment, the DSI pharmaceutical composition comprises omeprazole and at least one compound chosen from famotidine, cimetidine, ranitidine, and nizatidine.

One embodiment of the invention provides DSI pharmaceutical compositions comprising greater than about 50 mass % of an active pharmaceutical ingredient, such as omeprazole. In one embodiment, the DSI pharmaceutical composition comprises greater than about 60 mass % of omeprazole as an active pharmaceutical ingredient. In another embodiment, the DSI pharmaceutical composition comprises greater than about 70 mass % of an active pharmaceutical ingredient. In other embodiments, the DSI pharmaceutical composition comprises about 70-90 mass % of an active pharmaceutical ingredient or about 75-85 mass % of an active pharmaceutical ingredient.

For example, a DSI pharmaceutical composition o according to the invention may contain about 5-25 mass % bovine gelatin, 5-25 mass % mannitol, about 0-1 mass % of a surfactant, about 0-0.5 mass % of a flavorant and about 50-90 mass % of an active pharmaceutical ingredient. A preferred DSI formulation contains about 5-20 or 10-15 mass % bovine gelatin, about 5-20 or 10-15 mass % mannitol, about 0-0.7 mass % of a surfactant, about 0.001-0.4 mass % of a flavorant and about 65-85 mass % of anomeprazole. Also disclosed herein are products produced by the above-described methods. In one embodiment the product produced comprises about 70 mass % omeprazole. In one embodiment, a DSI pharmaceutical composition of omeprazole according to the invention may contain about 5-25 mass % bovine gelatin, 5-25 mass % mannitol, about 0-2 mass % of a surfactant, about 0-1 mass % of a flavorant and about 60-90 mass % of omeprazole. A preferred DSI formulation contains about 10-15 mass % bovine gelatin, 10-15 mass % mannitol, about 0.001-0.7 mass % of a surfactant, about 0.001-0.4 mass % of a flavorant and about 65-85 mass % of omeprazole. Also disclosed herein are products produced by the above-described methods. In one embodiment the product produced comprises about 70 mass % omeprazole.

In at least one embodiment, the methods of treatment described herein comprise administering the active ingredient (e.g., omeprazole) in a dehydrated form, such that the active ingredient is rapidly and efficiently delivered to the animal's circulatory system upon contact with the animal's natural biological fluids.

In one embodiment, the DSI pharmaceutical composition provides a Tmax of less than about 200 minutes. In another embodiment, the DSI pharmaceutical composition provides a Tmax of less than about 150 minutes. In another embodiment, the DSI pharmaceutical composition provides a Tmax of less than about 120 minutes. In another embodiment, the DSI pharmaceutical composition provides a Tmax of less than about 100 minutes. In another embodiment, the DSI pharmaceutical composition provides a Tmax of less than about 80 minutes. In another embodiment, the DSI pharmaceutical composition provides a Tmax of less than about 60 minutes. In another embodiment, the DSI pharmaceutical composition provides a Tmax of less than about 50 minutes. In another embodiment, the DSI pharmaceutical composition provides a Tmax of less than about 40 minutes. In another embodiment, the DSI pharmaceutical composition provides a Tmax of less than about 30 minutes.

In one embodiment, administering a DSI pharmaceutical composition as disclosed herein provides a first Tmax and a second Tmax. As used herein the term "first Tmax" refers to the first relative maximum for the blood concentration of the active pharmaceutical ingredient following administering a DSI pharmaceutical composition comprising that active pharmaceutical ingredient. As used herein the term "second Tmax" refers to the second relative maximum for the blood concentration of the active pharmaceutical ingredient following administering a DSI pharmaceutical composition comprising that active pharmaceutical ingredient. The first Tmax occurs when a portion of the DSI pharmaceutical composition is absorbed via the non-keratinous fibers or in a mucosal cavity, for example in the mouth. The second Tmax then may occur as the remainder of the DSI pharmaceutical composition is absorbed view the gastro-intestinal (GI) tract. In one embodiment, the first Tmax is less than about 150 minutes. In another embodiment, the first Tmax is less than about 120 minutes. In another embodiment, the first Tmax is less than about 100 minutes. In another embodiment, the first Tmax is less than about 80 minutes. In another embodiment, the first Tmax is less than about 60 minutes. In another embodiment, the first Tmax is less than about 40 minutes. In one embodiment, the second Tmax is less than about 200 minutes. In another embodiment, the second Tmax is less than about 180 minutes. In another embodiment, the second Tmax is less than about 160 minutes. In another embodiment, the second Tmax is less than about 140 minutes. In another embodiment, the second Tmax is less than about 120 minutes. In another embodiment, the second Tmax is less than about 100 minutes.

In one embodiment, when the active pharmaceutical ingredient is omeprazole, one dose of a DSI pharmaceutical composition provides a first Tmax and a second Tmax. In another embodiment, one dose of an omeprazole DSI pharmaceutical composition provides a first Tmax and a second Tmax. In another embodiment, a dose of an omeprazole DSI pharmaceutical composition provides a first Tmax between about 30-60 minutes and a second Tmax between about 120-160 minutes.

Disclosed herein are methods of controlling the production of digestive fluids, comprising administering an above-described the DSI pharmaceutical composition comprising omeprazole to an animal in need of treatment. In one embodiment, the animal is an equine. In another embodiment, the animal is a human. In one embodiment, the method controlling the production of digestive fluids comprises administering to the said animal a first peak in blood omeprazole concentration and a second peak in blood omeprazole concentration. In another embodiment, the administering a first peak in blood omeprazole concentration and a second peak in blood omeprazole concentration are achieved by administering one dose of omeprazole.

Disclosed herein are methods of treating or preventing gastric ulcers in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing gastric ulcers in an animal needing treatment comprises administering to the said animal a first peak in blood omeprazole concentration and a second peak in blood omeprazole concentration. In another embodiment, the administering a first peak in blood omeprazole concentration and a second peak in blood omeprazole concentration are achieved by administering one dose of omeprazole.

Disclosed herein are methods of treating or preventing duodenal ulcers in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing duodenal ulcers in an animal needing treatment comprises administering to the said animal a first peak in blood omeprazole concentration and a second peak in blood omeprazole concentration. In one embodiment, the administering a first peak in blood omeprazole concentration and a second peak in blood omeprazole concentration are achieved by administering one dose of omeprazole.

Disclosed herein are methods of treating or preventing Zollinger-Ellison syndrome in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing Zollinger-Ellison syndrome an animal needing treatment comprises administering to the said animal a first peak in blood omeprazole concentration and a second peak in blood omeprazole concentration. In one embodiment, the administering a first peak in blood omeprazole concentration and a second peak in blood omeprazole concentration are achieved by administering one dose of omeprazole.

Disclosed herein are methods of treating or preventing laryngopharyngeal reflux in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing laryngopharyngeal reflux in an animal needing treatment comprises administering to the said animal a first peak in blood omeprazole concentration and a second peak in blood omeprazole concentration. In one embodiment, the administering a first peak in blood omeprazole concentration and a second peak in blood omeprazole concentration are achieved by administering one dose of omeprazole.

Disclosed herein are methods of treating or preventing dyspepsia in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing dyspepsia in an animal needing treatment comprises administering to the said animal a first peak in blood omeprazole concentration and a second peak in blood omeprazole concentration. In one embodiment, the administering a first peak in blood omeprazole concentration and a second peak in blood omeprazole concentration are achieved by administering one dose of omeprazole.

Disclosed herein are methods of treating or preventing peptic ulcer disease in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing peptic ulcer disease in an animal needing treatment comprises administering to the said animal a first peak in blood omeprazole concentration and a second peak in blood omeprazole concentration. In one embodiment, the administering a first peak in blood omeprazole concentration and a second peak in blood omeprazole concentration is achieved by administering one dose of omeprazole.

Disclosed herein are methods of treating or preventing gastritis in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing gastritis in an animal needing treatment comprises administering to the said animal a first peak in blood omeprazole concentration and a second peak in blood omeprazole concentration. In one embodiment, the administering of a first peak in blood omeprazole concentration and a second peak in blood omeprazole concentration is achieved by administering one dose of omeprazole.

Disclosed herein are methods of treating or preventing gastroesophageal reflux disease in an animal needing treatment, comprising administering an above-described the DSI pharmaceutical composition comprising omeprazole to an animal in need of treatment. In one embodiment, the animal is an equine. In another embodiment, the animal is a human. In one embodiment, the method of treating or preventing gastroesophageal reflux disease in an animal needing treatment comprises administering to the said animal a first peak in blood omeprazole concentration and a second peak in blood omeprazole concentration. In one embodiment, the administering a first peak in blood omeprazole concentration and a second peak in blood omeprazole concentration is achieved by administering one dose of omeprazole.

Disclosed herein are methods of raising the pH in an animal's stomach comprising administering an above-described DSI pharmaceutical composition comprising omeprazole to the animal. In one embodiment, the animal is an equine. In another embodiment, the animal is a human. In one embodiment, the method of raising the pH of an animal's stomach comprises administering to the said animal a first peak in blood omeprazole concentration and a second peak in blood omeprazole concentration. In one embodiment, the animal is an equine. In another embodiment, the animal is a human. In one embodiment, the administering a first peak in blood omeprazole concentration and a second peak in blood omeprazole concentration is achieved by administering one dose of an omeprazole DSI pharmaceutical composition.

Disclosed herein are methods of making a DSI pharmaceutical composition comprising combining one or more active pharmaceutical ingredient(s) with one or more pharmaceutically inactive compound(s) to form a pre-formulation, freezing the pre-formulation, reducing the pressure surrounding the pre-formulation, and lyophilizing the pre-formulation. In one embodiment, the method comprises combining one or more active pharmaceutical ingredients with bovine gelatin and water to form a pre-formulation, freezing the pre-formulation, reducing the pressure surrounding the pre-formulation, and lyophilizing the pre-formulation to form a DSI pharmaceutical composition. In one embodiment, the method comprises combining one or more active pharmaceutical ingredients with bovine gelatin and water and also adding at least one compound chosen from mannitol, sucralose, a flavorant and a surfactant. In one embodiment, the method comprises combining omeprazole with bovine gelatin, mannitol and water to form a pre-formulation, adjusting the pH of that formulation to a basic pH (e.g., between about 8 to 9, between about 9 to 10, or between about 10 to 11 and preferably between about 8-8.5, or 8.3), freezing the pre-formulation, then reducing the pressure surrounding the pre-formulation and lyophilizing the pre-formulation to form a DSI pharmaceutical composition. The preformulation may also optionally contain a pharmaceutically acceptable surfactant, a flavorant and other additives and excipients known in the pharmaceutical and veterinary arts. The components of the pre-formulation may be dissolved together in a single solution or prepared as separate solutions that are then combined to make the pre-formulation.

In one embodiment, the pre-formulation comprises omeprazole, bovine gelatin, mannitol, and water in about the following relative proportions by mass: 40:7:6:200, respectively. For example, an omeprazole preformulation may contain about 1-10 mass % bovine gelatin, 1-10 mass % mannitol, about 0-0.5 mass % of a surfactant, about 0-0.2 mass % of a flavorant, about 10-30 mass % of omeprazole and about 45-90 mass % deionized (DI) water. A preferred preformulation contains about 3-5 mass % bovine gelatin, 3-5 mass % mannitol, about 0.1-0.3 mass % of a surfactant, about 0.05-0.15 mass % of a flavorant, about 15-25 mass % of omeprazole and about 55-75 mass % DI water. The amount of omeprazole in a DSI pharmaceutical composition of the invention many range from about 50 to 500 mg, preferably from about 100 to 300 mg, or be about 200 mg. In one embodiment, the DSI pharmaceutical composition produced by the above method has a mass % of omeprazole of between about 65 mass %-about 75 mass % omeprazole.

As mentioned above, pharmaceutically acceptable surfactants may be included in a DSI pharmaceutical composition of the invention. Exemplary surfactants include, but are not limited to, sodium lauryl sulfate (SLS), sodium docusate and PEG. For DSI pharmaceutical compositions with omeprazole an anionic surfactant such as sodium docusate is generally preferred. The surfactant aids in releasing the composition from a bubble pack, e.g., preventing it from sticking to the package surface. Mixtures of surfactants may be used in a DSI pharmaceutical composition of the invention.

Any flavorant used in pharmaceutical or veterinary formulations may be used. A mint flavor is one example. Fruit flavorants, such as citrus or cherry, are another example.

Advantageously, in at least some embodiments, DSI pharmaceutical compositions according to the disclosure may ensure complete and accurate dosing with less stress for both the animal and the animal handler. Further, the methods of the disclosure may allow for higher concentrations of active ingredients, thereby minimizing the need for multiple dosing.

Effective amounts may vary according to various factors, such as, but not limited to, the general health of the animal, the degree or severity of the particular disease under treatment, the age of the animal, the organs infected or infested, and the like. In at least one embodiment of the therapeutic methods disclosed herein, the amount of the DSI pharmaceutical composition is sufficient to provide therapeutic levels of the active ingredient as quickly as possible.

In one example, the active ingredient is omeprazole, the amount of said DSI pharmaceutical composition administered is that sufficient to provide about 0.5 mg/kg to about 8.0 mg/kg of active ingredient per body weight of the animal and about 1.0 mg/kg to about 6.0 mg/kg, about 4.0 mg/kg of active ingredient per body weight of the animal, with an approximate amount of about 5-700 mg omeprazole/dose, about 5-85 mg omeprazole/dose about 100-250 mg omeprazole/dose or about 350-550 mg omeprazole/dose, depending factors such as whether a low dose formulation or high dose formulation is needed and upon the animal being treated. For example, in humans omeprazole is administered in doses of 5, 10, 20, and 40 mg.

In another embodiment, the method disclosed herein comprises administering less than about 100 mg of omeprazole to the animal per day. In some embodiments, the methods disclosed herein comprise administering between about 1 mg to about 100 mg of omeprazole per day or between about 10 mg to about 80 mg of omeprazole per day. In some embodiments, the methods disclosed herein comprise administering between about 25 mg to about 75 mg of omeprazole per day.

In some embodiments, the methods and compositions of this disclosure comprise controlling the pH of an animal's stomach. For example, this disclosure includes methods of controlling the pH of an animal's stomach comprising administering omeprazole to an animal. As used herein the term controlling means maintaining a pH range that is healthy for the animal; maintaining does not necessarily include raising or lowering the pH to achieve the said healthy pH range.

In a further exemplary embodiment, the active ingredient is omeprazole and the amount of the DSI pharmaceutical composition administered is that sufficient to provide omeprazole at a pH of greater than about 6. In other exemplary embodiments, omeprazole is administered to the animal's non-keratinous fibers at a pH of about 10.

Animals suitable for treatment in the disclosed methods include homeothermic animals, for example, humans, equine, bovine, ovine, porcine, caprine, canine, feline or the like animals. For example, the disclosed methods would provide a benefit to any animal for whom the metabolic disposition of an active pharmaceutical ingredient is found problematic, or for which initial dose titration may pose risks, or which is otherwise undesirable.

The above disclosed doses and dosage ranges are not intended to be limiting. A practitioner skilled in the art may likewise administer suitable DSI pharmaceutical compositions (e.g., immediate or rapid release formulation) in single or divided doses, according to the desired therapeutic effect. Thus, in certain clinical situations it may be desirable to administer compositions to give initial high levels of the active ingredient, followed by lower dose maintenance doses.

EXAMPLES

The preparation and characterization of DSI pharmaceutical compositions of the invention are described below. The DSI pharmaceutical compositions described below were characterized using the following tests:

Dry weight—Weights of ten units were measured individually using an analytical balance to determine consistency of unit dosage.

Disintegration Time—This test determined the speed of which a DSI unit disintegrate in water maintained at 37.0° C.±0.5° C. Testing is carried out using a USP Disintegration Tester and a calibrated thermometer and timer.

Load to Fracture—This test was used to determine the force in Kg at which a DSI unit will break using TA-XT2 Texture Analyser 3-point bend test.

Appearance—The test evaluates the physical appearance of top and bottom surface of DSI units particularly relating to freeze drying defects such as melting, shrinkage of unit and cracking. Rating from 1 (the worst) to 10 (the best) are assigned after examination of 10 units.

Assay—To determine the % LC, testing was performed using Agilent 1100 and 1200 HPLC systems connected to a TotalChrom acquisition system for data collection and processing.

Example 1: DSI Pharmaceutical Composition of Omeprazole

DSI pharmaceutical compositions of the invention were prepared using omeprazole as the active pharmaceutical ingredient (API). The ingredients used to manufacture the DSI pharmaceutical compositions are listed in Table 1. Omeprazole was sourced from Srini Pharmaceuticals Limited, India, and all other materials were supplied by Catalent Pharmaceutical Solutions, LLC.

TABLE 1

List of Ingredients

| Ingredient | Function | Specification |
|---|---|---|
| Omeprazole | API | |
| Bovine Gelatin | Matrix former | USP |
| Mannitol | Bulking agent | USP |
| Docusate Sodium | Surfactant/Wetting Agent | USP |
| Mint Flavor | Flavor | Non-compendia |
| Purified Water (deionized water, DI water) | Vehicle | USP |
| Sodium Hydroxide | pH adjustment | ACS grade |

The DSI pharmaceutical composition was manufactured using the process described below. A 200 mg omeprazole DSI pharmaceutical composition was prepared. Table 2 lists the amount of each ingredient used.

Manufacturing Procedure:
1. Purified water was transferred to an appropriate sized beaker and heated to 60° C.±5° C.
2. Gelatin and mannitol were then added and mixed with a magnetic stir bar until completely dissolved to form a first solution.
3. The first solution was then cooled to about 30° C.
4. Purified water was transferred to a second beaker and heated to 45° C.±5° C. to allow the docusate sodium surfactant to rapidly dissolve when added.
5. Docusate Sodium was then added and mixed with a magnetic stir bar until completely dissolved to form a second solution.
6. The second solution was then cooled to room temperature (25° C.).
7. Omeprazole, as the API, was added to the second solution (prepared in step 5) and stirred for 1 hour.

8. Slowly added the first solution of gelatin and mannitol mix to the second solution of API mix and stirred for 1 hour.
9. If needed, sweetener and/or flavors were then added and stirred to mix for about 30 minutes.
10. pH adjustments to about 8.3±0.2 using Sodium Hydroxide.
11. Q.S. to final weight using purified water.
12. The solution/suspensions were stirred for at least 60 minutes prior to dispensing.
13. Dispensing was performed using an IVEK Dispenses 700 pump. Weight checks were performed initially at the set up stage as well as intermittently during dosing.
14. The solutions were dispensed into preformed blister trays having pocket sizes prepared using a Rohrer R550 tray former to hold 1000 mg of the solution.
15. The filled blister trays were frozen using an Air Products cryogenic freezer.
16. The frozen blisters were stored at a −30° C. set-point in a Revco freezer until used in freeze drying.
17. The frozen units were freeze dried at 45° C. (unless otherwise indicated) using a FTS Lyostar-II freeze dryer having three shelves.
18. The freeze dried units were handled in a low humidity manufacturing area and were sealed in Marvelseal 360 sachets using a Traco sealer.

TABLE 2

200 mg Omeprazole DSI Pharmaceutical Composition

| Ingredient | Wet Mass % | Wet Mass/Unit | Dry Mass % |
|---|---|---|---|
| Bovine gelatin | 3.5% | 35 mg | 13% |
| Mannitol | 3.0% | 30 mg | 11% |
| Sodium Docusate | 0.2% | 2 mg | 0.7% |
| Mint Flavor | 0.1% | 1 mg | 0.4% |
| Omeprazole | 20.0% | 200 mg | 75% |
| Purified (DI) Water | 73.2% | 732 mg | — |
| Total | 100% | 1000 mg | |

Batches of DSI pharmaceutical compositions containing 200 mg of omeprazole using the manufacturing process above with the batch variations described in Table 3. Units from each batch were characterized by Appearance, Load to Fracture and Disintegration Time. The results are reported in Tables 4-6, respectively.

TABLE 3

Batch Variations

| Batch Number | Batch Variations |
|---|---|
| 1-1 | 0.1% Surfactant<br>Freeze dried at 0.0° C. shelf temperature |
| 1-2 | 0.1% Surfactant<br>Freeze dried at 15.0° C. shelf temperature |
| 1-3 | 0.1% Surfactant<br>Freeze dried at −15.0° C. shelf temperature |
| 1-4 | 0.1% Surfactant<br>Freeze dried for 4 hours |
| 1-5 | 0.1% Surfactant<br>Freeze dried for 6 hours |
| 1-6 | 0.1% Surfactant<br>Freeze dried for 8 hours |

TABLE 4

Appearance Testing Results

| Batch Number | Rating | Appearance Description |
|---|---|---|
| 1-1 | 6 | White round tables with some collapse at the top and pitted marks with units sticking to foil |
| 1-2 | 6 | White round tables with some collapse at the top and pitted marks with units sticking to foil |
| 1-3 | 7 | White round tables with some collapse at the top |
| 1-4 | 6 | White round tables with some collapse at the top and minor cracking with units sticking to foil |
| 1-5 | 6 | White round tables with some collapse at the top and minor cracking with units sticking to foil |
| 1-6 | 6 | White round tables with some collapse at the top with units sticking to foil |

TABLE 5

Load to Fracture Results (Kg)

| | Batch Number | | | | | |
|---|---|---|---|---|---|---|
| Unit # | 1-1 | 1-2 | 1-3 | 1-4 | 1-5 | 1-6 |
| 1 | 0.565 | 0.801 | 0.685 | 0.754 | 0.889 | 0.640 |
| 2 | 0.638 | 0.708 | 0.779 | 0.655 | 0.759 | 0.837 |
| 3 | 0.566 | 0.753 | 0.639 | 0.580 | 0.893 | 0.656 |
| 4 | 0.595 | 0.727 | 0.778 | 0.678 | 0.837 | 0.717 |
| 5 | 0.544 | 0.907 | 0.907 | 0.659 | 0.898 | 0.766 |
| Avg. | 0.582 | 0.779 | 0.758 | 0.665 | 0.855 | 0.723 |

TABLE 6

Disintegration Time (seconds)

| | Batch Number | | | | | |
|---|---|---|---|---|---|---|
| Unit # | 1-1 | 1-2 | 1-3 | 1-4 | 1-5 | 1-6 |
| 1 | 2 | 8 | 2 | 3 | 3 | 2 |
| 2 | 3 | 10 | 2 | 2 | 3 | 2 |
| 3 | 2 | 11 | 3 | 2 | 2 | 3 |
| 4 | 2 | 13 | 2 | 3 | 3 | 2 |
| 5 | 3 | 11 | 2 | 2 | 2 | 2 |
| Max Time | 3 | 13 | 3 | 3 | 3 | 3 |

Example 2: Formulation Design of Experiments for DSI Pharmaceutical Compositions of Omeprazole A Design of Experiments (DOE) study was performed by manufacturing and testing nine batches on a 250 gram wet mass scale. The DOE study, using a 2 level, 3 factor design (8 experiments), varied three parameters: the amount of bovine gelatin, the amount of mannitol and the shelf temperature. A centerpoint experiment was added to the design for a total of 9 experiments. Table 7 describes the DOE study parameters in terms of the wet mass percent of bovine gelatin and mannitol and drying temperature.

TABLE 7

DOE Study Parameters (wet mass %)

| Experiment | Factor 1 (Gelatin) | Factor 2 (Mannitol) | Factor 3 (Drying Temp) |
|---|---|---|---|
| 2-6 | 4.5% | 2% | −15° C. |
| 2-1 | 4.5% | 2% | +15° C. |
| 2-4 | 4.5% | 4% | −15° C. |

TABLE 7-continued

DOE Study Parameters (wet mass %)

| Experiment | Factor 1 (Gelatin) | Factor 2 (Mannitol) | Factor 3 (Drying Temp) |
|---|---|---|---|
| 2-9 | 4.5% | 4% | +15° C. |
| 2-2 | 2.5% | 2% | −15° C. |
| 2-3 | 2.5% | 2 | +15° C. |
| 2-7 | 2.5% | 4% | −15° C. |
| 2-5 | 2.5% | 4% | +15° C. |
| 2-8 | 3.5% | 3% | 0° C. |

The manufacturing process of Example 1 was used with the following process parameters: (i) the freezing step was at −50° C. setpoint with a 3.3 minute cycle; (ii) in the freeze-drying, the unit loading was at −25° C. with a ramp rate of 1.5-2° C./min to reach primary drying set-point/375 mTorr; (iii) the primary drying was at −15° C., 0° C. or 15° C. shelf-temperature (these are the Low-Mid-High variables for the DOE) using constant vacuum of 375 mTorr and a time of 6 hours; and (iv) the secondary drying was at a ramp rate of 1.5-2° C./min to 22° C. The DOE outputs were three sets of physical data: Appearance (Table 8), Load to Fracture (Table 9) and Disintegration Time (Table 10).

Figure 2:
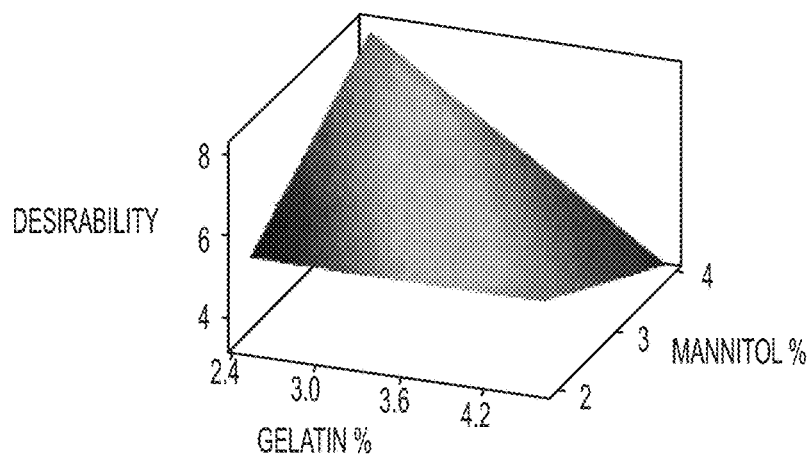
FIG. 2 depicts the DOE Response surface of Factors 1 & 2 (Factor 3 fixed at 0° C. shelf temperature) as described in Example 3.
Figure 3:
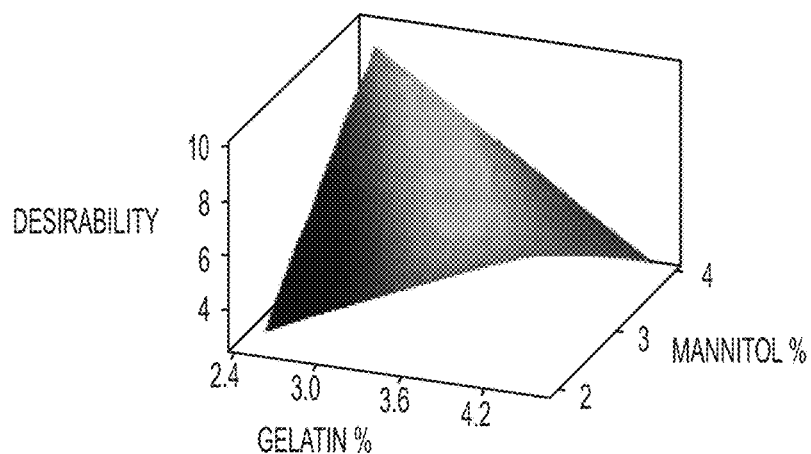
FIG. 3 depicts the DOE Response surface of Factors 1 & 2 (Factor 3 fixed at −15° C. shelf temperature) as described in Example 3.

The center-point batch (Experiment 8) yielded optimal physical data, with an Appearance rating of 10/10 and 3 second disintegration time. The DOE study did not yield data supporting a formulation change from the center-point batch. However, data analysis using Minitab® software (version 16.21) did identify a number of significant interactions. A single value of "Desirability" was determined based on the study outputs which are displayed on FIG. 1 (fixed shelf temp. of 15° C.), FIG. 2 (fixed shelf temp. of 0° C.) and FIG. 3 (fixed shelf temp. of −15° C.). This DOE study did show that (i) overall, changes in gelatin concentration have a much greater affect on desirability of the DIS pharmaceutical composition of omeprazole than changes in mannitol concentration; and (ii) low level freeze drying (shelf) temperature is most favorable, yielding the best desirability scores and also an apparent robust knowledge space at the centerpoint.

TABLE 8

DOE Appearance Testing Results

| Batch # | Rating | Appearance Description |
|---|---|---|
| 2-6 | 6 | White round tablets with some base melting and pitted units |
| 2-1 | 3 | White round tablets with a hollow layer above the base |
| 2-4 | 4 | White round tablets with significant base melting in almost all units |
| 2-9 | 3 | White round tablets with a hollow layer above the base |
| 2-2 | 4 | White round tablets that are very fragile and with cracks traversing the width of the tablets |
| 2-3 | 6 | White round tablets with some minor cracks and sticking to foil |
| 2-7 | 9 | White round tablets with rough surface but no other defects |
| 2-5 | 7 | White round tablets with some very minor cracks and sticking to foil |
| 2-8 | 10 | White round tablets free of defects |

TABLE 9

DOE Load to Fracture Results (Kg)

| | Batch Number | | | | | | | | |
|---|---|---|---|---|---|---|---|---|---|
| Unit # | 2-6 | 2-1 | 2-4 | 2-9 | 2-2 | 2-3 | 2-7 | 2-5 | 2-8 |
| 1 | 1.490 | 1.065 | 1.920 | 1.680 | 0.196 | 0.170 | 0.288 | 0.236 | 0.804 |
| 2 | 1.691 | 1.288 | 2.372 | 1.213 | 0.164 | 0.136 | 0.252 | 0.278 | 0.960 |
| 3 | 1.789 | 1.139 | 1.789 | 1.223 | 0.050 | 0.164 | 0.269 | 0.236 | 0.821 |
| 4 | 1.881 | 1.229 | 1.915 | 1.225 | 0.122 | 0.167 | 0.248 | 0.280 | 0.795 |
| 5 | 2.050 | 1.260 | 2.250 | 1.291 | 0.114 | 0.167 | 0.306 | 0.330 | 0.739 |
| Avg. | 1.780 | 1.196 | 2.049 | 1.326 | 0.129 | 0.161 | 0.273 | 0.272 | 0.824 |

TABLE 10

DOE Disintegration Testing Results (min:sec)

| | Experimental Number | | | | | | | | |
|---|---|---|---|---|---|---|---|---|---|
| Unit # | 2-6 | 2-1 | 2-4 | 2-9 | 2-2 | 2-3 | 2-7 | 2-5 | 2-8 |
| 1 | 0:05 | 0:31 | 1:28 | 0:26 | 1:55 | 0:02 | 0:01 | 0:05 | 0:03 |
| 2 | 0:05 | 0:27 | 1:31 | 0:23 | 1:12 | 0:01 | 0:02 | 0:04 | 0:03 |
| 3 | 0:05 | 0:31 | 1:27 | 0:22 | 1:28 | 0:02 | 0:02 | 0:05 | 0:03 |
| Max Time | 0:05 | 0:31 | 1:31 | 0:26 | 1:55 | 0:02 | 0:02 | 0:05 | 0:03 |

Example 3: Stability Studies of DSI Pharmaceutical Compositions of Omeprazole

Two batches of DSI pharmaceutical compositions of omeprazole, 200 mg unit, were manufactured using the method of Example 1 but at different pH of 7.96 and 8.47. The tablets were packaged in Marvel Seal 360 aluminum sachets with 4 trays of 8 tablets each (32 tablets). The DSI pharmaceutical compositions were placed on accelerated conditions to generate stability data. As is known in the art, omeprazole under certain aqueous conditions is chemically unstable. The DSI pharmaceutical compositions were stored at 25° C./60% RH and 40° C./75% RH storage conditions and tested on an initial (T=0), one month (T=1) and three month (T=3) time points. The testing included content uniformity (at initial time point (T=0) only) in compliance with USP <905>, Appearance, Assay, Disintegration and Load-to-fracture. The data for each batch 3-1 and 3-2 is reported in Tables 10, 11 and 12, respectively.

TABLE 10

Initial (T = 0) Content Uniformity

| Batch 3-1 | | Batch 3-2 | |
|---|---|---|---|
| Sample | % Content | Sample | % Content |
| 1 | 99.3 | 1 | 100.3 |
| 2 | 99.4 | 2 | 100.4 |
| 3 | 99.3 | 3 | 99.9 |
| 4 | 99.2 | 4 | 99.9 |
| 5 | 99.3 | 5 | 100.3 |
| 6 | 99.1 | 6 | 100.3 |
| 7 | 98.9 | 7 | 100.4 |
| 8 | 99.2 | 8 | 100.5 |
| 9 | 98.9 | 9 | 100.4 |
| 10 | 98.3 | 10 | 100.8 |
| Average | 99.1 | Average | 100.3 |
| Std. Dev. (SD) | 0.3 | Std. Dev. (SD) | 0.3 |
| % Rel. Std. Dev. (% RSD) | 0.3 | % Rel. Std. Dev. (% RSD) | 0.3 |
| Acceptance | 0.8 | Acceptance | 0.6 |

TABLE 10-continued

Initial (T = 0) Content Uniformity

| Batch 3-1 | | Batch 3-2 | |
|---|---|---|---|
| Sample | % Content | Sample | % Content |
| Value (AV) ≤L1% (L1 = 15.0) | | Value (AV) ≤L1% (L1 = 15.0) | |

TABLE 11

Stability Test Results, Batch 3-1

| | | Initial (T = 0) | | 1 Month (T = 1) | | 3 Month (T = 3) | |
|---|---|---|---|---|---|---|---|
| Test | Sample # | 25° C./60% RH | 40° C./75% RH | 25° C./60% RH | 40° C./75% RH | 25° C./60% RH | 40° C./75% RH |
| Appearance | | White, round tablets | White, round tablets | White, round tablets | White, round tablets | White, round tablets | White, round tablets |
| Assay | 1 | 99.2% LC | 99.2% LC | 98.8% LC | 98.8% LC | 99.6% LC | 99.6% LC |
| | 2 | 99.4% LC | 99.4% LC | 98.5% LC | 98.9% LC | 100.8% LC | 99.8% LC |
| | Average | 99.3% LC | 99.3% LC | 98.7% LC | 98.8% LC | 100.2% LC | 99.7% LC |
| Disintegration Time | 1 | 5 sec | 5 sec | 7 sec | 9 sec | 11 sec | 11 sec |
| | 2 | 6 sec | 6 sec | 10 sec | 8 sec | 11 sec | 10 sec |
| | 3 | 7 sec | 7 sec | 7 sec | 9 sec | 10 sec | 9 sec |
| | 4 | 6 sec | 6 sec | 11 sec | 9 sec | 11 sec | 11 sec |
| | 5 | 5 sec | 5 sec | 7 sec | 8 sec | 9 sec | 12 sec |
| | 6 | — | — | 12 sec | 9 sec | 11 sec | 11 sec |
| | Max | 7 sec | 7 sec | 12 sec | 9 sec | 11 sec | 12 sec |
| Load to Fracture | 1 | 0.800 Kg | 0.800 Kg | 0.705 Kg | 0.906 Kg | 0.758 Kg | 0.854 Kg |
| | 2 | 0.910 Kg | 0.910 Kg | 0.740 Kg | 0.804 Kg | 0.833 Kg | 0.864 Kg |
| | 3 | 0.795 Kg | 0.795 Kg | 0.814 Kg | 0.758 Kg | 0.811 Kg | 0.785 Kg |
| | 4 | 0.690 Kg | 0.690 Kg | 0.696 Kg | 0.967 Kg | 0.695 Kg | 0.833 Kg |
| | 5 | 1.215 Kg | 1.215 Kg | 0.593 Kg | 0.800 Kg | 0.901 Kg | 0.999 Kg |
| | Average | 0.882 Kg | | 0.710 Kg | 0.847 Kg | 0.800 | 0.867 Kg |

TABLE 12

Stability Test Results, Batch 3-2

| | | Initial (T = 0) | | 1 Month (T = 1) | | 3 Month (T = 3) | |
|---|---|---|---|---|---|---|---|
| Test | Sample # | 25° C./60% RH | 40° C./75% RH | 25° C./60% RH | 40° C./75% RH | 25° C./60% RH | 40° C./75% RH |
| Appearance | | White, round tablets | White, round tablets | White, round tablets | White, round tablets | White, round tablets | White, round tablets |
| Assay | 1 | 100.1% LC | 100.1% LC | 99.4% LC | 99.4% LC | 100.5% LC | 100.5% LC |
| | 2 | 100.1% LC | 100.1% LC | 99.6% LC | 99.8% LC | 100.5% LC | 100.8% LC |
| | Average | 100.1% LC | 100.1% LC | 99.5% LC | 99.6% LC | 100.5% LC | 100.7% LC |
| Disintegration Time | 1 | 4 sec | 4 sec | 9 sec | 6 sec | 11 sec | 9 sec |
| | 2 | 6 sec | 6 sec | 9 sec | 6 sec | 10 sec | 8 sec |
| | 3 | 6 sec | 6 sec | 8 sec | 8 sec | 7 sec | 7 sec |
| | 4 | 6 sec | 6 sec | 9 sec | 8 sec | 9 sec | 8 sec |
| | 5 | 4 sec | 4 sec | 8 sec | 6 sec | 10 sec | 8 sec |
| | 6 | — | — | 8 sec | 7 sec | 8 sec | 7 sec |
| | Max | 6 sec | 6 sec | 9 sec | 8 sec | 11 sec | 9 sec |
| Load to Fracture | 1 | 0.667 Kg | 0.667 Kg | 0.975 Kg | 0.606 Kg | 0.800 Kg | 0.651 Kg |
| | 2 | 0.840 Kg | 0.840 Kg | 0.792 Kg | 0.620 Kg | 0.833 Kg | 0.743 Kg |
| | 3 | 0.799 Kg | 0.799 Kg | 0.953 Kg | 0.982 Kg | 0.899 Kg | 0.890 Kg |
| | 4 | 1.097 Kg | 1.097 Kg | 0.574 Kg | 0.623 Kg | 0.667 Kg | 0.880 Kg |
| | 5 | 0.737 Kg | 0.737 Kg | 0.886 Kg | 0.657 Kg | 0.754 Kg | 0.701 Kg |
| | Average | 0.828 Kg | 0.828 Kg | 0.836 Kg | 0.698 Kg | 0.791 Kg | 0.773 Kg |

In the compositions and methods described herein, where a particular compound is recited, applicants contemplate isolated enantiomers and mixtures thereof in any proportions. For example, where the only one stereoisomer is stated for a particular stereocenter, applicants contemplate any possible stereoisomer at that position. For example, where the compound omeprazole is used, it should be understood that applicants contemplate either pure isomer and/or any mixture thereof.

It is to be understood that the foregoing description is exemplary and explanatory only, and not to be interpreted as restrictive of the disclosure.

Various modifications of this disclosure, in addition to those shown and described herein, will become apparent to those skilled in the art from the following examples and the foregoing description. Such modifications are also intended to fall within the scope of the present disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a pharmaceutically active ingredient" or "a therapeutic agent" is intended to mean at least one therapeutic agent. Unless otherwise indicated, all numbers or ranges used in the specification and claims are to be understood as being modified in all instances by the term "about," whether or not so stated. It should also be understood that the precise numerical values used in the specification and claims form additional embodiments of the disclosure, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

The claimed invention is:

1. A method of treating gastric ulcers, duodenal ulcers, Zollinger-Ellison syndrome, laryngopharyngeal reflux, dyspepsia, peptic ulcer disease, gastritis, or gastroesophageal reflux in an animal needing treatment, comprising administering an effective amount of a pharmaceutical composition for direct systemic introduction (DSI) to the animal, wherein the pharmaceutical composition for DSI comprises: about 10-17 dry mass % bovine gelatin, about 10-17 dry mass % mannitol, about 0-1 dry mass % of a surfactant, about 0-0.5 dry mass % of a flavorant, and about 65-80 dry mass % of omeprazole.

2. The method of claim 1, wherein the pharmaceutical composition for DSI comprises: about 10-13 dry mass % bovine gelatin, about 12-15 dry mass % mannitol, and about 0.1-0.3 dry mass % of a surfactant.

3. The method of claim 1, wherein the pharmaceutical composition for DSI has a disintegration time of 7 seconds or less in deionized water maintained at 37.0° C.±0.5° C.

4. The method of claim 1, wherein the pharmaceutical composition for DSI has a disintegration time of 4 seconds or less in deionized water maintained at 37.0° C.±0.5° C.

5. The method of claim 1, wherein the animal is equine.

6. The method of claim 1, wherein the animal is human.

7. The method of claim 1, wherein the pharmaceutical composition for DSI is delivered to the animal via the animal's non-keratinous tissues comprising the step of placing the pharmaceutical composition for DSI into a mucosal cavity of the animal.

8. The method of claim 7, wherein the mucosal cavity is selected from an oral cavity, an anal cavity, a vaginal cavity, a nasal cavity, a gingival mucosa, a lingual mucosa, a palatal mucosa, a pharyngeal mucosa, a sublingual mucosa, and a non-gastric mucosa.

9. The method of claim 8, wherein the mucosal cavity is an oral cavity.

10. The method of claim 1, wherein gastric ulcers are treated.

11. The method of claim 1, wherein duodenal ulcers are treated.

12. The method of claim 1, wherein Zollinger-Ellison syndrome is treated.

13. The method of claim 1, wherein laryngopharyngeal reflux is treated.

14. The method of claim 1, wherein dyspepsia is treated.

15. The method of claim 1, wherein peptic ulcer disease is treated.

16. The method of claim 1, wherein gastritis is treated.

17. The method of claim 1, wherein gastroesophageal reflux is treated.

* * * * *